United States Patent [19]

Matsunaga et al.

[11] Patent Number: 4,929,762

[45] Date of Patent: May 29, 1990

[54] PROCESS FOR PRODUCING A PHENOL AND/OR A CYCLOHEXANONE

[75] Inventors: Fujihisa Matsunaga; Hiroshi Fukuhara, both of Chiba, Japan

[73] Assignee: Mitsui Petrochemical Industries, Ltd., Tokyo, Japan

[21] Appl. No.: 318,117

[22] Filed: Mar. 2, 1989

[30] Foreign Application Priority Data

Mar. 7, 1988 [JP] Japan ................................. 63-53071

[51] Int. Cl.$^5$ .............................................. C07C 45/00
[52] U.S. Cl. .................................... 568/361; 568/799; 568/343
[58] Field of Search ....................... 568/361, 799, 343

[56] References Cited

U.S. PATENT DOCUMENTS

| | | | |
|---|---|---|---|
| 2,503,641 | 4/1950 | Taylor et al. ........................ | 568/799 |
| 3,149,166 | 9/1964 | Poehler et al. ....................... | 568/361 |
| 3,256,348 | 6/1966 | Schlossman ......................... | 568/799 |
| 3,534,110 | 10/1970 | Juguin et al. ......................... | 568/799 |
| 3,801,651 | 4/1974 | Adolphen et al. .................... | 568/799 |

FOREIGN PATENT DOCUMENTS

| | | | |
|---|---|---|---|
| 2107395 | 8/1977 | Fed. Rep. of Germany ...... | 568/362 |
| 3314372 | 10/1984 | Fed. Rep. of Germany ...... | 568/799 |
| 49-35365 | 4/1974 | Japan .................................. | 568/799 |
| 62-255443 | 11/1987 | Japan .................................. | 568/799 |

Primary Examiner—James H. Reamer
Attorney, Agent, or Firm—Nixon & Vanderhye

[57] ABSTRACT

A phenol and/or a cyclohexanone is prepared by dehydrogenation of cyclohexenone and/or a cyclohexenol in liquid phase under the presence of a solid catalyst comprising a platinum-group metal loaded on a carrier. The solid catalyst comprises a carrier selected from activated carbon and hydrotalcites.

6 Claims, No Drawings

PROCESS FOR PRODUCING A PHENOL AND/OR A CYCLOHEXANONE

BACKGROUND OF THE INVENTION

This invention is directed to a process for producing a phenol and/or a cyclohexanone, and more particularly, it is directed to a process for producing a phenol which is useful as an intermediate in the production of phenolic resins, plasticizers, dyes, and the like, and a cyclohexanone which is useful as an intermediate in the production of high molecular weight compounds such as Nylon and polyesters, and organic chemicals such as plasticizers and synthetic lubricates.

Phenols have been produced, for example, by dehydrogenating cyclohexanones or cyclohexanols under gas-phase reaction conditions by using a platinum based catalyst as described in Japanese Patent Application Kokai No. 44-6810.

Cyclohexanones have been produced by oxidizing cyclohexenones under particular reaction conditions.

Several processes for simultaneously producing phenols and cyclohexanones have been known. Japanese Patent Application Kokai No. 51-88929 discloses an oxidation of cyclohexylbenzene with oxygen under the presence of catalysts such as hydrobromic and hydrochloric acids to produce a phenol and a cyclohexanone. U.S. Pat. No. 4,021,490 discloses an automatic oxidation of cyclohexylbenzene to produce cyclohexylbenzene hydroperoxide, which is further decomposed with an acid to simultaneously produce a phenol and a cyclohexanone.

Conventional processes for producing phenols and/or cyclohexanones suffer from their low yield of the resulting products.

The cyclohexylbenzene which is generally used in conventional processes for simultaneously producing a phenol and a cyclohexanone is not readily available.

In the process of Japanese Patent Application Kokai No. 51-88929, the hydrobromic or hydrochloric acid employed as the catalyst was liable to corrode equipment used in the process. In the process of U.S. Pat. No. 4,021,490, the hydroperoxide produced as an intermediate was chemically unstable and required special equipments for the sake of safe operation, resulting in a complicated production system.

It is therefore an object of the present invention to provide a process wherein a phenol and/or a cyclohexanone is safely produced at high yield.

Other objects and advantages of the invention will become apparent as the description thereof proceeds.

SUMMARY OF THE INVENTION

The foregoing objects are achieved by an improved process for producing a phenol and/or a cyclohexanone wherein a cyclohexenone and/or a cyclohexenol is dehydrogenated in liquid phase under the presence of a solid catalyst comprising a platinum-group metal loaded on a carrier. The solid catalyst may preferably comprise a carrier selected from activated carbon and hydrotalcites. And preferably the loading metal is palladium.

DETAILED DESCRIPTION OF THE INVENTION

The cyclohexenones which may be used in the process of the present invention include cyclohexenone-2, 4-methylcyclohexenone-2, 3-methylcyclohexenone-2, etc. The cyclohexenols which may be used in the present invention include 3-hydroxycyclohexene, 3-hydroxy-6-methylcyclohexene, 1-methyl-3-hydroxycyclohexene, etc. The cyclohexenone and the cyclohexenol may either be used alone or in a combination of two or more.

The solid catalyst comprising a platinum-group metal loaded on a carrier used in accordance with the present invention is a granular or a powdery catalyst which constitutes a nonhomogeneous solid phase in the liquid phase reaction system.

The solid catalyst may preferably comprise a carrier selected from activated carbon and hydrotalcites, and at least one member selected from the group consisting of palladium, ruthenium and platinum loaded on the carrier. Among these metals palladium is preferred.

The solid catalyst comprising at least one metal selected from palladium, ruthenium and platinum loaded on activated carbon may either be prepared by a conventional loading process or purchased from a commercial source.

The solid catalyst comprising at least one metal selected from palladium, ruthenium and platinum loaded on a hydrotalcite may preferably be prepared by loading the platinum-group metal onto the hydrotalcite.

The hydrotalcite which may be used as the carrier in the present invention include various hydrotalcites as well as compounds which generate a hydrotalcite structure by hydration. The hydrotalcite may preferably be a hydrotalcite or an oxide solid solution thereof prepared by calcining the hydrotalcite, which generate a hydrotalcite structure by hydration.

An aqueous solution of a salt of the platinum-group metal at a predetermined concentration is added to a dispersion of the hydrotalcite in water at once. The mixture is agitated so that metal ions of the salt of the platinum-group metal may be adsorbed on the hydrotalcite carrier through ion exchange. During the agitation, the mixture may be heated in order to accelerate the ion exchange between the salt and the hydrotalcite.

The salt of the platinum-group metal employed for the preparation of the catalyst may be selected from salts of mineral acids such as chlorides, nitrates, and sulfates; and complex salts such as acetylacetonato and ammine complex salts.

The metal ion adsorbed on the hydrotalcite is reduced to the metal state to produce the platinum-group metal-loaded hydrotalcite.

The reduction of the metal ion to metal state may generally be carried out by conventional processes employed for reducing compounds of platinum-group metals including a reduction in gas phase by hydrogen, and a reduction in liquid phase by hydrogen or appropriate chemical reducing agents such as $NaBH_4$ and formalin. Among these reduction processes, a reduction in gas or liquid phase by hydrogen is particularly preferred.

The solid catalyst employed in the process of the present invention may generally include from 3 to 15% by weight, preferably from 5 to 10% by weight of the platinum-group metal based on the total weight of the solid catalyst.

The amount of the solid catalyst used is generally in the range of from 0.5 to 10% by weight, and preferably from 2 to 5% by weight based on the raw materials charged.

A reaction solvent may be employed in the process according to the present invention to promote the dehydrogenation reaction. The solvents which may be employed include any desired solvents which are inert under the dehydrogenating conditions, for example, aromatic hydrocarbons such as benzene, toluene, xylene, etc; aliphatic hydrocarbons such as pentane, hexane, heptane, etc.; and alicyclic hydrocarbons such as cyclopentane, cyclohexane, methylcyclohexane, etc.

The dehydrogenation reaction may generally be carried out at a temperature of from 150° C. to 330° C., and preferably from 200° C. to 280° C.

The dehydrogenation reaction may be carried out at any reaction pressure as long as the reaction system is maintained in liquid phase. Since the reaction system may preferably be oxygen free, it is preferable to purge the reaction system with an inert gas such as nitrogen by exerting an appropriate pressure before effecting the dehydrogenation reaction.

The dehydrogenation reaction in accordance with the present invention is generally carried out in a continuous or a batch operation by suspending the solid catalyst in the liquid phase. However, the dehydrogenation reaction may also be carried out in such a system as a fixed-bed catalytic reactor.

The present invention is further described by referring to the following Examples. It is to be understood that the present invention is by no means limited by these Examples.

EXAMPLE 1

An autoclave equipped with an induction rotary agitator having an internal volume of 30 ml was charged with 4.9 g of a mixture of 45% cyclohexenol, 52% cyclohexenone and 3% others, 19.5 g of toluene, and 0.54 g of 5% Pd/C (5% Pd carbon powder manufactured by NIPPON ENGELHALD LTD.). The autoclave was purged with nitrogen and the pressure was raised to 10 kgf/cm$^2$ in a nitrogen atmosphere. The reaction was effected at 250° C. for 2 hours with agitation. After the reaction had completed, the reaction mixture was taken out of the autoclave and the catalyst was separated by filtration. A quantitative analysis with gas chromatography of the reaction product revealed that phenol and cyclohexanone were produced at yields of 35.0% and 40.5%, respectively, and byproducts of benzene and cyclohexane were produced at yields of 9.2% and 3.3%, respectively, based on the total weight of the cyclohexenol and the cyclohexenone charged.

EXAMPLE 2

The procedure of Example 1 was repeated except that 5% Pt/C (5% Pt carbon powder manufactured by NIPPON ENGELHALD LTD.) was used for the reaction catalyst, and the reaction temperature was raised to 300° C. An analysis of the resulting product revealed that phenol and cyclohexanone were produced at yields of 28.8% and 33.6%, respectively.

EXAMPLE 3

The procedure of Example 1 was repeated at 250° C. for 2hours except that 5% Ru/C (5% Ru carbon powder manufactured by NIPPON ENGELHALD LTD.) was used for the reaction catalyst, An analysis of the resulting product revealed that phenol and cyclohexanone were produced at yields of 26.8% and 31.0%, respectively.

EXAMPLE 4

[Preparation of dehydrogenation catalyst]

A separable flask equipped with an agitator was charged with 5 g of hydrotalcite (KW-1000, manufactured by KYOWA CHEMICAL INDUSTRY CO., LTD.) and 150 ml of deionized water. The mixture was agitated at room temperature. To this mixture, 150 ml of aqueous solution of palladium nitrate containing 0.5 g of palladium nitrate was added at once. The mixture was agitated for 2 hours at room temperature, heated to 80° C. and agitated for further 2 hours to completely adsorb palladium ion onto the hydrotalcite. The mixture was then centrifuged to separate the solid hydrotalcite onto which palladium ion is adsorbed from the remaining liquid components. The resulting solid was charged in a titanium autoclave having an interior volume of 500 ml together with 150 ml of 1N aqueous sodium hydroxide, and agitated to effect reduction with hydrogen at 150° C. under an elevated pressure of 350 kgf/cm$^2$ for 8 hours. A palladium catalyst loaded on hydrotalcite was thus prepared.

[Dehydrogenation reaction]

The procedure of Example 1 was repeated at 250° C. for 2 hours except that 0.5 g of the thus prepared palladium catalyst was used for the reaction catalyst. An analysis of the resulting product revealed that phenol and cyclohexanone were produced at yields of 35.0% and 41.0%, respectively.

As apparent from the above described results, a phenol and/or a cyclohexanone is safely produced from a cyclohexenone and/or a cyclohexenol at high yield as well as high selectivity.

We claim:

1. A process for producing a phenol, a cyclohexanone or both wherein a cyclohexenone and a cyclohexenol are dehydrogenated in liquid phase under the presence of a solid catalyst comprising a platinum-group metal loaded on a carrier.

2. The process according to claim 1, wherein said solid catalyst comprises a carrier selected from activated carbon and/or hydrotalcites, or combinations thereof.

3. The process according to claim 1, wherein said platinum-group metal is palladium.

4. A process for producing a phenol, a cyclohexanone or both wherein a cylcohexenol is dehydrogenated in liquid phase under the presence of a solid catalyst comprising a platinum group metal loaded on a carrier.

5. The process according to claim 4, wherein said solid catalyst comprises a carrier selected from activated carbon, hydrotalcites or combinations thereof.

6. The process according to claim 4, wherein said platinum-group metal is palladium.

* * * * *